(12) United States Patent
Miller et al.

(10) Patent No.: US 7,507,864 B2
(45) Date of Patent: Mar. 24, 2009

(54) METHOD FOR THE SYNTHESIS OF CURCUMIN ANALOGUES

(75) Inventors: Jeffrey Christopher Miller, Salisbury, MD (US); Miguel O. Mitchell, Salisbury, MD (US)

(73) Assignee: Salisbury University, Salisbury, MD (US)

( * ) Notice: Subject to any disclaimer, the term of this patent is extended or adjusted under 35 U.S.C. 154(b) by 0 days.

(21) Appl. No.: 11/782,405

(22) Filed: Jul. 24, 2007

(65) Prior Publication Data

US 2008/0033055 A1 Feb. 7, 2008

Related U.S. Application Data

(60) Provisional application No. 60/821,011, filed on Aug. 1, 2006.

(51) Int. Cl.
*C07C 45/00* (2006.01)
(52) U.S. Cl. ........................ 568/313; 568/325
(58) Field of Classification Search ................. 568/313, 568/325; 514/679
See application file for complete search history.

(56) References Cited

U.S. PATENT DOCUMENTS

| 3,479,345 | A | 11/1969 | Geschickter et al. |
| 5,679,864 | A | 10/1997 | Krackov et al. |
| 6,790,979 | B2 | 9/2004 | Lee et al. |
| 2007/0060644 | A1 * | 3/2007 | Vander Jagt et al. .......... 514/475 |

FOREIGN PATENT DOCUMENTS

WO   WO2006089894   8/2006

OTHER PUBLICATIONS

Garcia-Alloza, M. et al. (e-pub Apr. 2007) "Curcumin Labels Amyloid Pathology In Vivo, Disrupts Existing Plaques, And Partially Restores Distorted Neurites In An Alzheimer Mouse Model," J. Neurochem. 10.1111/j.1471-4159.2007.04613.x.
Ono, K. (2006) "The Development of Preventives and Therapeutics for Alzheimer's Disease that Inhibit the Formation of β-Amyloid Fibrils (fAβ), as Well as Destabilize Preformed fAβ," Curr. Pharma. Des. 12:4357-4375.
Ono. K. et al. (2004) "Curcumin Has Potent Anti-Amyloidogenic Effects For Alzheimer's Beta-Amyloid Fibrils in vitro," J. Neurosci. Res. 75, 742-750.
Lim, G.P. et al. (2001) "The Curry Spice Curcumin Reduces Oxidative Damage And Amyloid Pathology In An Alzheimer Transgenic Mouse,". J. Neurosci. 21:8370-8377.
Ramassamy, C. (2006) "Emerging Role Of Polyphenolic Compounds In The Treatment Of Neurodegenerative Diseases: A Review Of Their Intracellular Targets," Eur. J. Pharmacol. 545(1):51-64.
Yang, F. et al. (2005) "Curcumin Inhibits Formation Of Amyloid Beta Oligomers And Fibrils, Binds Plaques, And Reduces Amyloid in vivo," J. Biol. Chem. 280:5892-5901.
Pedersen et al. (1985) "Synthesis of Naturally Occurring Curcuminoids and Related Compounds," Chem. Abstract. 103:178092.
Nurfina, A.N. et al. (1997) Synthesis Of Some Symmetrical Curcumin Derivatives And Their Anti-Inflammatory Activity, Eur. J. Med. Chem. 32:321-328).
Arieta, A.F. (1994) Abstract. "Direct Synthesis of Demethoxycurcumin," C.R. Acad. Sci. Paris, Ser II, 479-482.
Arrieta, A.F. et al. (1991) Abstract. "Synthesis and H-NMR-Spectroscopic Investigatons of New Curcumin Analogs," J. Prakt. Chem. 334:656-700.
Roughly et al. (1973) "Experiments in the Biosynthesis of Curcumin," J. Chem. Soc. Perkins Tran I, I, 23:79-88.
Park, S.Y. et al. (2002) ("Discovery Of Natural Products From Curcuma longa That Protect Cells From Beta-Amyloid Insult: A Drug Discovery Effort Against Alzheimer's Disease," J. Nat. Prod. 65(9):1227-1231).
Gomes, Dde C. et al. (2002) Abstract. "Total Synthesis And Anti-Leishmanial Activity Of Some Curcumin Analogues," Arzneimittelforschung. 52(9):695-698).
Cole G.M. et al. (2004) "NSAID And Antioxidant Prevention Of Alzheimer's Disease: Lessons From In Vitro And Animal Models," Ann. N.Y. Acad. Sci. 1035:68-84).
Ringman, J.M. et al. (2005) "A Potential Role of the Curry Spice Curcumin in Alzheimer's Disease," Curr. Alzheimer's Res. 2(2): 131-136.

\* cited by examiner

*Primary Examiner*—Sikarl A Witherspoon
(74) *Attorney, Agent, or Firm*—Jeffrey I. Auerbach; Edell, Shapiro & Finnan, LLC

(57) ABSTRACT

The present invention relates to improved methods for achieving the synthesis of 1,7-diaryl-1,6-heptadiene-3,5-diones, and in particular curcumin and its analogues. The invention provides a process for synthesizing such compounds in substantial yield and purity using environmentally benign processes and materials. The invention also relates to the use of such synthesized products in the treatment of Alzheimer's Disease and other diseases.

9 Claims, 5 Drawing Sheets

US 7,507,864 B2

METHOD FOR THE SYNTHESIS OF CURCUMIN ANALOGUES

CROSS-REFERENCE TO RELATED PATENT APPLICATIONS

This application claims priority to U.S. Patent Application Ser. No. 60/821,011, filed on Aug. 1, 2006, which application is herein incorporated by reference in its entirety.

FIELD OF THE INVENTION

The present invention relates to improved methods for achieving the synthesis of 1,7-diaryl-1,6-heptadiene-3,5-diones, and in particular curcumin and its analogues. The invention also relates to the use of such synthesized products in the treatment of Alzheimer's Disease and other diseases.

BACKGROUND OF THE INVENTION

Alzheimer's Disease is a chronic illness that is age-related in nature. It causes neurological degeneration due to genetic and environmental factors predisposing those afflicted. The disease is characterized by progressive memory loss, cognitive deterioration and behavioral disorders is the most common cause of dementia among elderly people (Goedert, M. et al. (2006) "*A Century Of Alzheimer's Disease*," Science. 314 (5800):777-781; Pallas, M. et al. (2006) "*Molecular And Biochemical Features In Alzheimer's Disease*," Curr Pharm Des. 12(33):4389-4408; Roberson, E. D. et al. (2006) "100 *Years And Counting: Prospects For Defeating Alzheimer's Disease*," Science. 314(5800):781-784; Samanta, M. K. et al. (2006) "*Alzheimer Disease And Its Management: A Review*." Amer. J. Ther. 13(6):516-526). Alzheimer's Disease is diagnosed in postmortem analysis by the presence of neurofibrillary tangles, senile plaques, and neuronal loss (Selkoe D. J. (1994) "*Alzheimer's Disease: A Central Role For Amyloid*," J. Neuropathol. Exp. Neurol. 53:438-447).

The best understood cause for the onset of Alzheimer's Disease is that the disease results from a misfolding and accumulation of two neuronal proteins: the amyloid beta ("Aβ") protein which is a proteolytic byproduct of the transmembrane protein amyloid precursor protein (APP) and microtubule-associated proteins known as "tau" proteins (Blurton-Jones, M. et al. (2006) "*Pathways By Which Abeta Facilitates Tau Pathology*," Curr. Alzheimer Res. 3(5):437-448; Golde, T. E. et al. (2006) "*Filling The Gaps In The Aβ Cascade Hypothesis Of Alzheimer's Disease*," Curr. Alzheimer Res. 3(5):421-430; Leissring M A. (2006) "*Proteolytic Degradation Of The Amyloid Beta-Protein: The Forgotten Side Of Alzheimer's Disease*," Curr. Alzheimer Res. 3(5):431-435; Ohyagi, Y. et al. (2006) "*Intracellular Amyloid Beta-Protein And Its Associated Molecules In The Pathogenesis Of Alzheimer's Disease*," Mini Rev. Med. Chem. 6(10):1075-1080; Urbanc, B. et al. (2006) "*Computer Simulations Of Alzheimer's Amyloid Beta-Protein Folding And Assembly*," Curr. Alzheimer Res. 3(5):493-504). Multiple isoforms of Aβ have been identified, ranging from 39-43 amino acid residues in length; the most common isoforms are Aβ40 and Aβ42. The loss of the body's ability to inhibit the mutation of the Aβ peptide occurs in a cascading effect.

The causes of Alzheimer's disease are not purely genetic predisposition. It has also been shown that people who have experienced multiple head injuries or have received high amounts of dietary cholesterol for extended periods are more susceptible to the disease (Canevari, L. et al. (Epub 2006 Dec. 27) "*Alzheimer's Disease And Cholesterol: The Fat Connection*," Neurochem Res. 32(4-5):739-750). Factors that may be responsible for a decreased susceptibility to the disease include uptake of estrogens, statins, and non-steroidal anti-inflammatory drugs (Cole G. M. et al. (2004) "*NSAID And Antioxidant Prevention Of Alzheimer's Disease: Lessons From In Vitro And Animal Models*," Ann. N.Y. Acad. Sci. 1035:68-84).

The site believed to be responsible for the initial onset of the misfolding proteins is the Aβ(1-42) peptide. A specific mutation or other defect is believed to cause the excessive polymerization of tau proteins from the neural fibrillary tangles. In essence the misfolding of these proteins has a toxic effect on enzymes responsible for correcting the mutating cells. The Aβ(25-35) site has been identified as the toxic fragment of βA(1-42) which causes this neuronal insult to PC12 cells (Park, S. Y. et al. (2002) "*Discovery Of Natural Products From Curcuma longa That Protect Cells From Beta-Amyloid Insult. A Drug Discovery Effort Against Alzheimer's Disease*," J. Nat. Prod. 65(9):1227-1231). Once the process has begun, the increased production of Aβ might not be necessary for the toxic effects to increase. Once initiated the polymerized tau proteins will continue to tangle and grow, degenerating neural function as they polymerize. This causes an increased accumulation of excessively tangled fibrils to the point where enzymes can no longer breakdown defective cells and neural pathways begin to degenerate at an increasing rate (Cole G. M. et al. (2004) "*NSAID And Antioxidant Prevention Of Alzheimer's Disease: Lessons From In Vitro And Animal Models*," Ann. N.Y. Acad. Sci. 1035:68-84). Treatments for Alzheimer's Disease currently involve the use of non-steroidal anti-inflammatory agents to slow the cascading effect of the disease's progression. To date, no fully successful therapy for Alzheimer's Disease has been developed.

Curcumin is a yellow pigment extracted from the rhizome of the plant *Curcuma longa*. The compound has been found to have a number of pharmacological activities, and represents a hopeful approach for delaying or preventing the progression of Alzheimer's Disease (Cole G. M. et al. (2004) "*NSAID And Antioxidant Prevention Of Alzheimer's Disease: Lessons From In Vitro And Animal Models*," Ann. N.Y. Acad. Sci. 1035:68-84; Bala, K. et al. (2006) "*Neuroprotective And Anti-Ageing Effects Of Curcumin In Aged Rat Brain Regions*," Biogerontology 7:81-89). In vitro studies have shown that curcumin attenuates inflammatory response of brain microglial cells (Jung K. K. et al. (2006) "*Inhibitory Effect Of Curcumin On Nitric Oxide Production From Lipopolysaccharide-Activated Primary Microglia*," Life Sci. 79:2022-2031; Kim H. Y. et al. (2003) "*Curcumin Suppresses Janus Kinase-STAT Inflammatory Signaling Through Activation Of Src Homology 2 Domain-Containing Tyrosine Phosphatase 2 In Brain Microglia*," J. Immunol. 171:6072-6079). Curcumin has also been reported to inhibit the formation of Aβ oligomers and fibrils in vitro (Ono, K. et al. (2004) "*Curcumin Has Potent Anti-Amyloidogenic Effects For Alzheimer's Beta-Amyloid Fibrils in vitro*," J. Neurosci. Res. 75, 742-750; Yang, F. et al. (2005) "*Curcumin Inhibits Formation Of Amyloid Beta Oligomers And Fibrils, Binds Plaques, And Reduces Amyloid in vivo*," J. Biol. Chem. 280:5892-5901), to prevent neuronal damage (Shukla P. K. et al. (2003) "*Protective Effect Of Curcumin Against Lead Neurotoxicity In Rat*," Hum. Exp. Toxicol. 22:653-658), and reduce oxidative damage (Lim, G. P. et al. (2001) "*The Curry Spice Curcumin Reduces Oxidative Damage And Amyloid Pathology In An Alzheimer Transgenic Mouse*,". J. Neurosci. 21:8370-8377) and amyloid accumulation (Yang, F. et al. (2005) "*Curcumin Inhibits Formation Of Amyloid Beta Oligomers And Fibrils, Binds Plaques, And Reduces Amyloid in vivo," J. Biol. Chem. 280: 5892-5901).

Curcumin has also been found to have anticancer activity, anti-inflammatory activity and immunomodulatory activity (McDonald, R et al. (2001) "Synthesis And Anticancer Activity Of Nordihydroguaiaretic Acid (NDGA) And Analogues," Anti-Cancer Drug Design 16(6):261-270; Parveen, I., et al. (2000) "Labeled Compounds of Interest as Antitumor Agents," Chem. Abstract. 133:281645; Martono, S. (1996) "Inhibitory Effects of Curcumin and its Analogs on In Vitro Rat Liver Glutathione S-Transferases Activity," Chem. Abstract. 128:110377; McDonald et al. (2001) "Synthesis and Anticancer Activity of nordihydrogualaretic Acid and Analogues, Chem. Abstract. 138:362138 (2001); Choshi et al. (1992) "Synthesis of Dibenzoylmethane Derivatives and Inhibition of Mutagenicity in Salmonella typhimurium," Chem. Abstract. 117:48036; Artiser, J. L. et al. (1998) "Curcumin Is an In Vivo Inhibitor of Angiogenesis," Molec. Med. 4:376-383; Ishida, J. et al. (2000) "Antitumor-Promoting Effects Of Cyclic Diarylheptanoids On Epstein-Barr Virus Activation And Two-Stage Mouse Skin Carcinogenesis," Canc. Lett. 159:135-140; Ruby, A. J., et al. (1995) "Anti-Tumour And Antioxidant Activity Of Natural Curcuminoids," Canc. Lett. 94:79-83; Sugiyama, Y. et al. (1996) "Involvement of the β-Diketone Moiety in the Antioxidantive Mechanism of Tetrahydrocurcumin," Biochem. Pharmacol. 52:519-525 (1996); Syu, Wan-Jr, et al. (1998) "Cytotoxicity of Curcuminoids and Some Novel Compounds from Curcuma zedoaria," J. Nat. Prod. 61:1531-1534; Gautam, S. C. et al. (2007) "Immunomodulation By Curcumin," Adv. Exp. Med. Biol. 595:321-341).

Pharmacological uses of curcumin are reviewed by Garcia-Alloza, M. et al. (e-pub April 2007) "Curcumin Labels Amyloid Pathology In Vivo, Disrupts Existing Plaques, And Partially Restores Distorted Neurites In An Alzheimer Mouse Model," J. Neurochem. 10.1111/j.1471-4159.2007.04613.x; Lim, G. P. et al. (2001) "The Curry Spice Curcumin Reduces Oxidative Damage And Amyloid Pathology In An Alzheimer Transgenic Mouse,". J. Neurosci. 21:8370-8377; Ono, K. (2006) "The Development of Preventives and Therapeutics for Alzheimer's Disease that Inhibit the Formation of β-Amyloid Fibrils (fAβ), as Well as Destabilize Preformed fAβ," Curr. Pharma. Des. 12:4357-4375; Ono, K. et al. (2004) "Curcumin Has Potent Anti-Amyloidogenic Effects For Alzheimer's Beta-Amyloid Fibrils in vitro," J. Neurosci. Res. 75, 742-750; Ramassamy, C. (2006) "Emerging Role Of Polyphenolic Compounds In The Treatment Of Neurodegenerative Diseases. A Review Of Their Intracellular Targets," Eur. J. Pharmacol. 545(1):51-64; Ringman, J. M. et al. (2005) "A Potential Role Of The Curry Spice Curcumin In Alzheimer's Disease," Curr. Alzheimer Res. 2(2): 131-136; and Yang, F. et al. (2005) "Curcumin Inhibits Formation Of Amyloid Beta Oligomers And Fibrils, Binds Plaques, And Reduces Amyloid in vivo," J. Biol. Chem. 280:5892-5901.

Clinical trials with curcumin have shown that the compound is not only safe but may be a chemoprotective (Cheng A. L. et al. (2001) "Phase I Clinical Trial Of Curcumin, A Chemopreventive Agent, In Patients With High-Risk Or Pre-Malignant Lesions," Anticancer Res. 21: 2895-2900) and anti-inflammatory (Holt P. R. et al. (2005) "Curcumin Therapy In Inflammatory Bowel Disease: A Pilot Study," Dig. Dis. Sci. 50:2191-2193) drug.

The isolation of natural curcumin from the Curcuma longa rhizome has proven to be difficult and costly (U.S. Pat. No. 5,679,864 (Krackov et al.); U.S. Pat. No. 6,790,979 (Lee et al.); Pedersen et al. (1985) "Synthesis of Naturally Occurring Curcuminoids and Related Compounds," Chem. Abstract. 103:178092 (1985); Nurfina, A. N. et al. (1997) "Synthesis Of Some Symmetrical Curcumin Derivatives And Their Anti-Inflammatory Activity, Eur. J. Med. Chem. 32:321-328). Krakov et al. disclose the synthesis of curcumin by reacting the enol form of a 2,4-diketone with a monocarbocyclic aldehyde in the presence of an organic amine catalyst. The reactants are dissolved in a highly polar, aprotic organic solvent. The curcumin-related product is recovered in crystalline form by precipitation from the reaction mass and solvent recrystallization. Other approaches to curcumin synthesis include aldol condensation of vanillin (3-methoxy-4-hydroxybenzaldehyde) and 2,4-pentanedione. However, the yields of product from such synthesis are reported to be very low, in large part because of the difficult and complicated procedures required for isolation and purification of the product. Methods for synthesizing curcumin and its analogues are disclosed in: WO06089894; and in Arieta, A. F. (1994) "Direct Synthesis of Demethoxycurcumin," C. R. Acad. Sci. Paris, Ser II, 479-482; Pedersen et al. (1985) "Synthesis of Naturally Occurring Curcuminoids and Related Compounds," Ann. Chem. 15:57-69; Arrieta, A. F. et al. (1991) "Synthesis and H-NMR-Spectroscopic Investigatons of New Curcumin Analogs," J. Prakt. Chem. 334:656-700; and Roughly et al. (1973) "Experiments in the Biosynthesis of Curcumin," J. Chem. Soc. Perkins Trans I, I, 23:79-88. Yields or process operability are reported to be poor (U.S. Pat. No. 5,679,864 (Krackov et al.)).

Despite all prior advances, available methods for synthesizing curcumin and its analogues remain labor intensive, time consuming and environmentally unfavorable especially for low purity products. Thus, a need remains for improved methods of synthesizing such compounds. The present invention is directed to this and related needs

SUMMARY OF THE INVENTION

The present invention relates to improved methods for achieving the synthesis of 1,7-diaryl-1,6-heptadiene-3,5-diones, and in particular curcumin and its analogues. The invention provides a process for synthesizing such compounds in substantial yield and purity using environmentally benign processes and materials. The invention also relates to the use of such synthesized products in the treatment of Alzheimer's Disease and other diseases.

In detail, the invention provides a method of synthesizing a curcuminoid comprising incubating a solution of an aryl aldehyde in the presence of a solution of a pentanedione under conditions sufficient to permit a hydrolysis reaction to occur thereby producing the curcuminoids;

wherein:
(A) the solution of an aryl aldehyde comprises a tri-alkyl borate, a boron oxide, and an alkylamine; and
(B) the pentanedione is dissolved in a lower alkyl ester.

The invention additionally concerns the embodiment of the above-described method wherein the pentanedione is 2,4-pentanedione; wherein the alkylamine is butylamine; or wherein the tri-alkyl borate is tri-butyl borate. The invention additionally concerns the embodiments of the above-described methods wherein: the pentanedione is 2,4-pentanedione and the alkylamine is butylamine; the pentanedione is 2,4-pentanedione and the tri-alkyl borate is tri-butyl borate; or the alkylamine is butylamine and the tri-alkyl borate is tri-butyl borate. The invention additionally concerns the embodiments of the above-described methods wherein the pentanedione is 2,4-pentanedione, the alkylamine is butylamine; and the tri-alkyl borate is tri-butyl borate.

The invention additionally concerns the embodiments of the above-described methods wherein the lower alkyl ester is selected from the group consisting of ethyl acetate, propyl acetate, butyl acetate (especially isobutyl acetate) and ethyl butyrate.

The invention additionally concerns a method for producing curcumin wherein: (A) the aryl aldehyde is 4-hydroxy-3-methoxybenzaldehyde; (B) the tri-alkyl borate is tri-butyl borate; (C) the alkylamine is butylamine; (D) the pentanedione is 2,4-pantanedione; and (E) the lower alkyl ester is ethyl acetate. The invention additionally concerns curcumin produced through any of the above-described methods.

The invention additionally concerns a method for producing bisdemethoxycurcumin wherein: (A) the aryl aldehyde is p-hydroxybenzaldehyde; (B) the tri-alkyl borate is tri-butyl borate; (C) the alkylamine is butylamine; (D) the pentanedione is 2,4-pantanedione; and (E) the lower alkyl ester is isobutyl acetate. The invention additionally concerns bisdemethoxycurcumin produced through any of the above-described methods.

The invention also concerns pharmaceutical compositions comprising the above-prepared curcuminoids (especially wherein the curcuminoids is curcumin or bisdemethoxycurcumin) or a salt or derivative thereof, and a pharmaceutically acceptable carrier. The invention particularly concerns such pharmaceutical compositions wherein said composition comprises a therapy for Alzheimer's Disease, for cancer, for an inflammatory disease, or for immunomodulation.

DESCRIPTION OF PREFERRED EMBODIMENTS OF THE INVENTION

Figure 1:
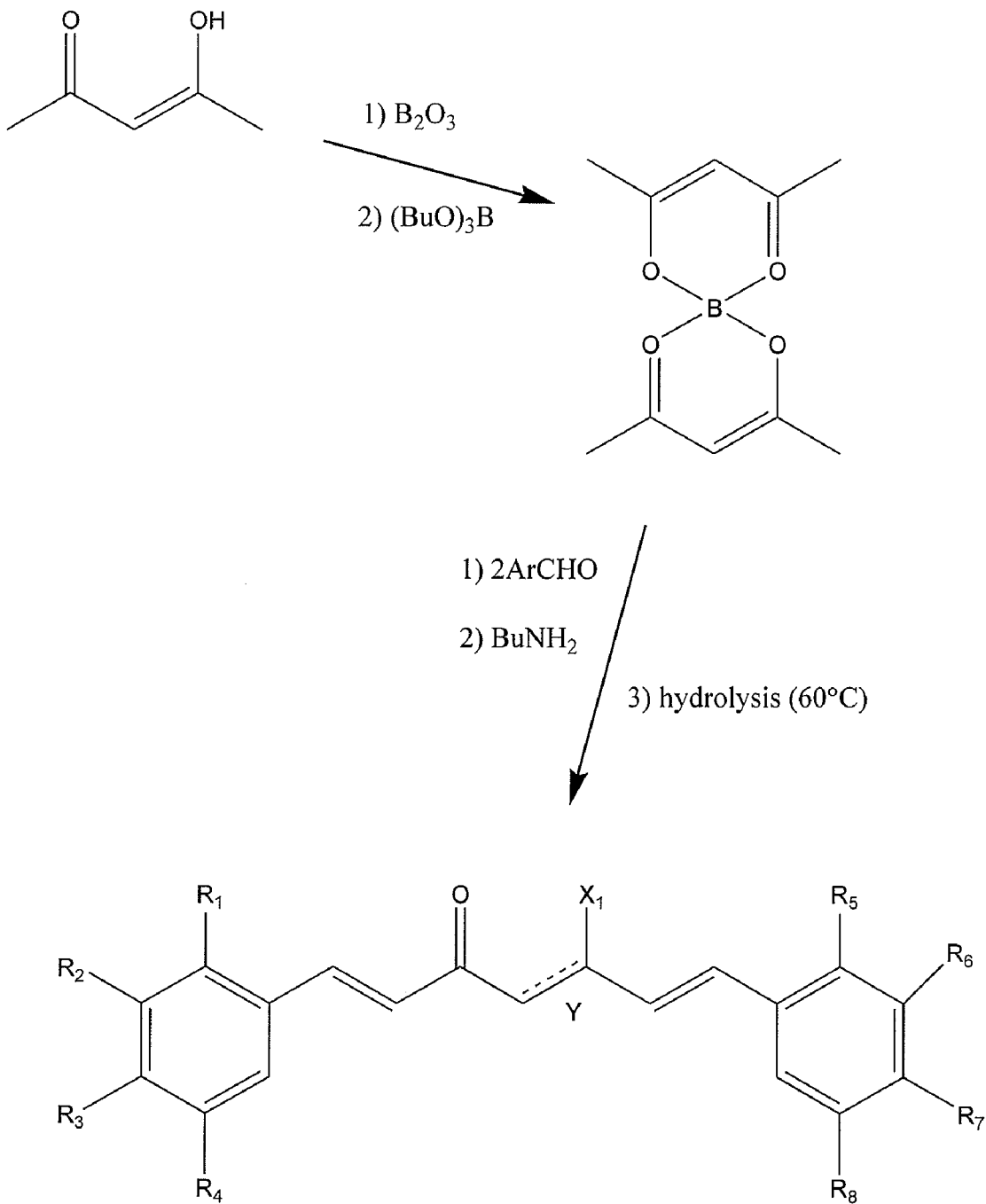
FIG. 1 shows the general scheme of a preferred embodiment of the synthesis methods of the present invention. $R_1$ and $R_5$ are independently selected from the group consisting of hydrogen or lower alkyl; $R_2$ and $R_6$ are independently selected from the group consisting of alkoxy, nitro, amino and dialkylamino; $R_3$ and $R_7$ are independently selected from the group consisting of hydroxyl, alkoxy, and —$OR_9C(O)R_{10}$, where $R_9$ is lower alkene and $R_{10}$ is alkoxy; or wherein $R_2$ and $R_3$ together are alkenedioxy, or wherein $R_6$ and $R_7$ together are alkenedioxy; $X_1$ is hydroxyl or a carbonyl oxygen, and Y is a single bond when $X_1$ is a carbonyl oxygen, and a double bond when $X_1$ is hydroxyl.

The present invention relates to improved methods for achieving the synthesis of 1,7-diaryl-1,6-heptadiene-3,5-diones, and in particular curcumin and its analogues. The invention provides a process for synthesizing such compounds in substantial yield and purity using environmentally benign processes and materials. The invention also relates to the use of such synthesized products in the treatment of Alzheimer's Disease and other diseases.

Curcumin (diferuloyl methane; 1,7-bis(4-hydroxy-3-methoxyphenyl)-1,6-heptadiene-3,5-dione) is a naturally occurring compound which is the main coloring principle found in the rhizomes of the plant *Curcuma longa* (U.S. Pat. No. 5,679,864 (Krackov et al.)). The 3,5-dione moiety can be readily protonated/deprotonated, and the terms curcumin and curcuminoids as used herein includes the 3,5-dione and the 3-cabonyl, 5-hydroxy tautomers of the molecule:

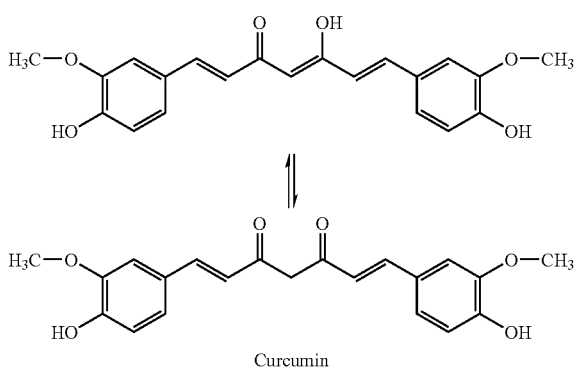

Curcumin

As used herein the term "curcuminoids" refers to structural analogues of curcumin having the general formula of 1,7-diaryl-1,6-heptadiene-3,5-diones (U.S. Pat. No. 6,790,979 (Lee et al.); U.S. Pat. No. 3,479,345 (Geschickter, C. F.)), and the general structure:

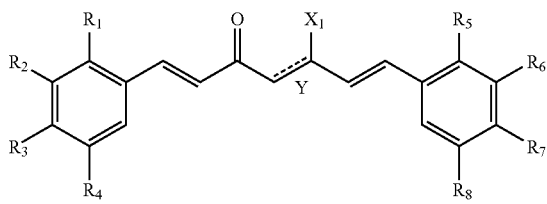

wherein $R_1$ and $R_5$ are independently selected from the group consisting of hydrogen or lower alkyl; $R_2$ and $R_6$ are independently selected from the group consisting of alkoxy, nitro, amino and dialkylamino; $R_3$ and $R_7$ are independently selected from the group consisting of hydroxyl, alkoxy, and —$OR_9C(O)R_{10}$, where $R_9$ is lower alkene and $R_{10}$ is alkoxy; or wherein $R_2$ and $R_3$ together are alkenedioxy, or wherein $R_6$ and $R_7$ together are alkenedioxy; $X_1$ is hydroxyl or a carbonyl oxygen, and Y is a single bond when $X_1$ is a carbonyl oxygen, and a double bond when $X_1$ is hydroxyl.

As used herein, the term "alkyl" or "lower alkyl" refers to C1, C2, C3, C4, C5, C6, C7 or C8 alkyl, which may be linear or branched and saturated or unsaturated. The term "alkoxy" as used herein refers to linear or branched, saturated or unsaturated oxo-hydrocarbon chains, including for example methoxy, ethoxy, propoxy, isopropoxy, butoxy, and t-butoxy. "Alkenyl" or "lower alkenyl" as used herein likewise refers to C1 to C4 alkenyl, and alkoxy or lower alkoxy as used herein likewise refers to C1 to C4 alkoxy. The term "alkylamino" as used herein refers to C1 to C4 linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc. The term "alkylenedioxy" refers to a group of the general formula —OR'O—, —OR'OR'—, or —R'OR'OR'— where each R' is independently alkyl.

Examples of such curcuminoids include demethoxycurcumin (p-hydroxy-cinnamoyl-feruloyl methane) and bisdemethoxycurcumin (1,7-bis-(4-hydroxyphenyl)-1,6-heptadiene-3,5-dione), and their respective 3-carbonyl, 5-hydroxy or 3-hydroxy, 5-carbonyl tautomers:

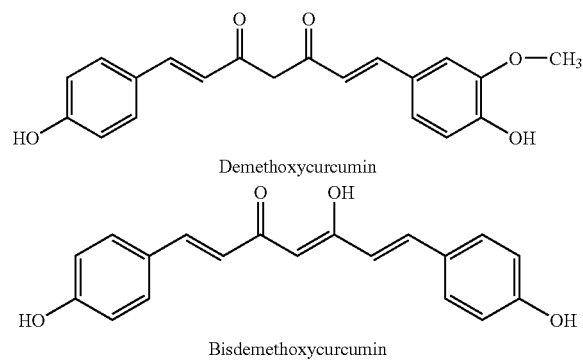

The use of curcuminoids, a previously researched family of anti-tumor compounds, has been proposed as a possible treatment for Alzheimer's disease. Curcuminoids have been found to have antioxidant, anti-inflammatory, and cholesterol lowering properties (Gomes, DdeC. et al. (2002) "*Total Synthesis And Anti-Leishmanial Activity Of Some Curcumin Analogues*," Arzneimittelforschung. 52(9):695-698). Curcumin appears to be an Aβ inhibitor capable of protecting cells from the effects of degraded and misfolded proteins. Animal studies have found it to be capable of attenuating inflammation, cellular oxidative damage and synaptic marker loss. Its restorative effects to Aβ infused human tau proteins in mice shows marked protection against mutant tau proteins and improved memory function. The beneficial effects of curcuminoids have been found at many stages of neural degeneration thus demonstrating its potential as not only a protective agent, but a regenerative one (Cole G. M. et al. (2004) "*NSAID And Antioxidant Prevention Of Alzheimer's Disease: Lessons From In Vitro And Animal Models*," Ann. N.Y. Acad. Sci. 1035:68-84).

The two most effective curcuminoids for the inhibition of plaque formation have been found to be demethoxycurcumin and bisdemethoxycurcumin (Park, S. Y. et al. (2002) "*Discovery Of Natural Products From Curcuma longa That Protect Cells From Beta-Amyloid Insult: A Drug Discovery Effort Against Alzheimer's Disease*," J. Nat. Prod. 65(9):1227-1231).

Bisdemethoxycurcumin is of particular interest to the present invention. Most studies involving its use do not provide pure samples. Extractions from the natural product, turmeric, are the most common sources of curcuminoids. Purification is accomplished using extensive chromatographic extraction and is a very labor intensive endeavor that does not provide a very pure material suitable for pharmacological use.

U.S. Pat. No. 5,679,864 (Krackov et al.) disclose a process for the synthesis of curcuminoids that involve the use of relatively expensive components that require intensive removal of impurities that require treatment for their disposal. Other methods for the synthetic production of curcumin from the starting products vanillin and 2,4-pentanedione involve the use of tri-butyl borate, boron oxide, and butylamine in a hydrolysis reaction with N,N-dimethylacetamide as a solvent and recrystallization using acetonitrile (U.S. Pat. No. 5,679,864 (Krackov et al.)).

The present invention substantially decreases problems associated with the recovery, waste disposal, and toxicity of such processes by replacing the employed solvents with fragrant esters that are known to have benign health effects and are used as flavoring agents in foods. The fragrant esters isobutyl acetate and ethyl butyrate are preferred for this purpose. These esters have been chosen as replacement solvents in the synthesis of curcumin analogues due to their solvency of starting materials and relatively low boiling point for removal. This is an improvement over other methods for synthetic production of curcumin and its analogues which require chromatography for solvent separations. This change in procedure lowers the costs associated with solvent purchase and disposal, toxicity of compounds used, and work-hours necessary for the chromatographic separations involved. Lowering the toxicity of all chemicals used alleviates the possibility that impurities present could cause adverse health effects, and allows for a negligible environmental impact.

The general scheme of a preferred embodiment of the synthesis methods of the present invention is shown in FIG. 1. A pentanedione is dissolved in a lower alkyl ester. The solution is then incubated with a solution of an aryl aldehyde that has been dissolved in a tri-alkyl borate, a boron oxide, and an alkylamine under conditions sufficient to permit a hydrolysis reaction to occur. 2,4-pentanedione is preferred, and may be dissolved in any of a variety of lower alkyl esters. Ethyl acetate, propyl acetate, butyl acetate (and especially isobutyl acetate) or ethyl butyrate are preferred lower alkyl esters. The aryl aldehyde will be determined in light of the curcumin whose synthesis is desired (for example, 4-hydroxy-3-methoxybenzaldehyde is preferably employed if the desired curcuminoids is curcumin; p-hydroxybenzaldehyde is preferably employed the desired curcuminoids is bisdemethoxycurcumin. Tri-butyl borate is a preferred trialkyl borate. Butylamine is a preferred alkylamine.

Thus, in accordance with the methods of the present invention, a solution of vanillin (4-hydroxy-3-methoxybenzaldehyde), butylamine, boron oxide and tri-butyl borate is prepared and then slowly added to a solution of 2,4-pentanedione dissolved ethyl acetate in order to achieve the synthesis of curcumin. For the synthesis of bisdemethoxycurcumin, reaction is permitted between a solution of p-hydroxybenzaldehyde, butylamine, boron oxide and tri-butyl borate and a solution of 2,4-pentanedione dissolved in isobutyl acetate.

After reaction has occurred, the materials are cooled to room temperature, rinsed with mild organic acid (e.g., aqueous acetic acid), and filtered. Recrystallization of the dried crude curcumin is performed with the a fragrant ester (e.g., the same ester as is employed to dissolve the 2,4-pentanedione. Rotary evaporation may be employed to remove the solvent, thereby providing the desired product.

Curcumin is a bright red product once purified and maintains the vanilla fragrance due to the presence of methoxy groups from the starting product vanillin. It is soluble in acetone, ethyl acetate, ethanol, and isobutyl acetate. The solubility of bisdemethoxycurcumin, however, is slightly different. It is very soluble in ethanol and isobutyl acetate but acetone and ethyl acetate solubility is limited. Bisdemethoxycurcumin maintains a pumpkin-orange appearance and is more crystalline in nature than curcumin.

During the initial synthesis of curcumin, solubility was apparent with several more favorable reaction solvents such as acetone, ethyl acetate, ethanol, and methanol. The replacement of N,N-dimethylacetamide with a more favorable solvent with a lower boiling point for a more feasible removal was attractive and intended to have the added benefit of it being both recoverable and reusable. The selection of fragrant esters as solvents such as isobutyl acetate and ethyl butyrate were more favorable than the use of acetone, ethanol, methanol, or ethyl acetate due to their low boiling points and extensive usage as flavoring agents. Isobutyl acetate and ethyl butyrate have boiling points of 116-117.5 and 120° C. respectively. Their use as flavoring agents is relative to the industrial process of curcuminoid synthesis due to the inherent nature of their minimal toxicity, recoverability, lowered purchasing and disposal costs due to their environmentally benign nature.

As discussed below, $^1$H and $^{13}$C NMR were used extensively with obtained melting points to determine the overall purity and determination of structure for both curcumin and bisdemethoxycurcumin. The obtained melting point for the curcumin crystals was found to be consistent with that reported by Park, S. Y. et al. (2002) ("*Discovery Of Natural Products From Curcuma longa That Protect Cells From Beta-Amyloid Insult: A Drug Discovery Effort Against Alzheimer's Disease*," J. Nat. Prod. 65(9):1227-1231). The melting point values of bisdemethoxycurcumin were significantly lower than that of the literature values, but were sharp melting points. This suggests that they are pure compound, but the most reasonable explanation for the inconsistency with literature values may be due to the crystal structure formation used for melting point determination in the literature reference. The literature reference used a "yellow needle" crystalline structure isolated from natural turmeric for the determination of melting point. $^1$H NMR analysis does not show the presence of p-hydroxybenzaldehyde in the final spectra, therefore the structure is very pure in content.

The curcumin and curcumin analogues of the present invention are useful as pharmaceutically active agents and may be utilized in bulk form. More preferably, however, these compounds are formulated into pharmaceutical formulations for administration. Any of a number of suitable pharmaceutical formulations (e.g., see Remington's Pharmaceutical Sciences, 19$^{th}$ Edition, A. R. Gennaro, ed., Mack Publishing Co., Easton, Pa. (1995), incorporated herein by reference in its entirety) may be utilized as a vehicle for the administration of the compounds of the present invention. Such compounds are preferably administered in "pharmacologically acceptable" amounts in the treatment of Alzheimer's Disease and other diseases (especially inflammatory diseases, immune disorders and cancers). A composition is said to be "pharmacologically acceptable" if its administration can be tolerated by a recipient patient. The administration of such compounds may be for either a "prophylactic" or "therapeutic" purpose. The compositions of the present invention are said to be administered for a "therapeutic" purpose if the amount administered is physiologically significant to provide a therapy for an actual manifestation of the disease. When provided therapeutically, the compound is preferably provided at (or shortly after) the identification of a symptom of actual disease. The therapeutic administration of the compound serves to attenuate the severity of such disease or to reverse its progress. The compositions of the present invention are said to be administered for a "prophylactic" purpose if the amount administered is physiologically significant to provide a therapy for a potential disease or condition. When provided prophylactically, the compound is preferably provided in advance of any symptom thereof. The prophylactic administration of the compound serves to prevent or attenuate any subsequent advance of the disease.

The curcumin and curcumin analogues of the present invention can be administered in conventional solid or liquid pharmaceutical administration forms, for example, as uncoated or (film-) coated tablets, capsules, powders, granules, suppositories or solutions. The active substances can, for this purpose, be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases. Such compositions may be the curcuminoids resulting from the processes of the invention, or may be a derivative (such as an acid, base, esterified, etc. derivative of such curcuminoids) or a pharmaceutically salt of such curcuminoid. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

The therapeutic compositions obtained in this way typically contain from about 0.1% to about 90% by weight of the active substance. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. Methods of use of curcumin and curcumin analogues are described by U.S. Pat. No. 6,790,979 (Lee et al.), herein incorporated by reference.

Having now generally described the invention, the same will be more readily understood through reference to the following examples, which are provided by way of illustration and are not intended to be limiting of the present invention unless specified.

EXAMPLE 1

Synthetic Methods of Curcumin

The synthesis of curcumin employed vanillin and 2,4-pentanedione and the use of tri-butyl borate, boron oxide, and butylamine in a hydrolysis reaction with ethyl acetate as the reaction solvent. First, 3.51 g of 2,4-pentanedione was dissolved with 5.0 mL of ethyl acetate in a separatory funnel. Approximately 11.04 g of vanillin, 1.03 g butylamine, 2.33 g boron oxide, and 18.80 mL of tri-butyl borate were added to a 500 mL round bottom flask and were dissolved in roughly 35 mL of ethyl acetate. When the temperature of the contents within the round bottom flask reached 70° C. and appeared to have dissolved significantly, slow addition to the round bottom flask of the separatory funnel containing 2,4-pentanedione was begun. The reaction was allowed to take place overnight once reaction temperature appeared to be stable. The following day the remaining solvent was easily removed and recovered by rotary evaporation. Then the reaction was allowed to cool to room temperature before rinsing the flask with a 100 mL solution of 5% aqueous acetic acid. The solution was allowed to sit for an hour then vacuum filtered. The recrystallization of the dried crude curcumin was performed with ethyl acetate and very mild heating (35-40° C.). Rotary evaporation was used to remove the solvent, providing 7.562 g of curcumin.

EXAMPLE 2

Synthetic Methods of Bisdemethoxycurcumin

The synthesis of bisdemethoxycurcumin from p-hydroxybenzaldehyde with 2,4-pentanedione, tri-butyl borate, boron oxide, and butylamine was performed with the use of isobutyl acetate as a reaction solvent since the solubility of bisdemethoxycurcumin in ethyl acetate is less effective. Approximately 6.520 g of p-hydroxybenzaldehylde was dissolved in isobutyl acetate with 9.260 g of tri-butyl borate, 1.426 g boron oxide, and 0.638 of butylamine in a 500 mL round bottom flask. The slow addition of 2.092 g of 2,4-pentanedione dissolved in a minimal amount of isobutyl acetate to the reaction flask occurred over the course of several hours. The reaction was sustained overnight at 80° C. and the solvent removal with rotary evaporation was performed. The product was rinsed with a 5% acetic acid solution and vacuum filtered. Upon drying, the solution was resuspended in water and filtered once again. The dry compound was triterated/recrystallized with the use of 95% ethanol and was precipitated with the addition of water. The original triteration did not prove to have adequately purified the sample by proton NMR therefore the triteration was repeated and the remaining ethanol was removed by drying the sample extensively. The procedure yielded 2.41 g of purified bisdemethoxycurcumin.

EXAMPLE 3

Analysis of Products

The initial synthesis of curcumin with ethyl acetate as both a reaction and crystallization solvent provided a 58.15% yield of 7.562 g. Initial synthesis of bisdemethoxycurcumin (Example 2; "Batch 1") had a total yield of 1.035 g and percent yield of 20.79%, using ethyl acetate as a solvent, but this recovery required a column filtration that was both time consuming and lowered percent recovery. Upon repeating the synthesis of bisdemethoxycurcumin using isobutyl acetate as solvent ("Batch 2"), it was possible to obtain 1.703 g of total purified product with a 32.73% yield. This simply involved a trituration of the product in 95% ethanol and precipitation with the addition of water. A second batch synthesis of bisdemethoxycurcumin was attempted with isobutyl acetate as a solvent on a larger scale with absolute ethanol for the trituration. This modification provided an overall yield of 2.41 g of product for a 37.43% yield. The curcumin melting point obtained was 179-180° C., which was very similar to the published melting point of 180-181° C. The bisdemethoxycurcumin melting point for the two batches of product was 217-218° C. and 216-217° C., respectively. This was significantly lower than the published melting point of 232-233° C.

Figure 2:
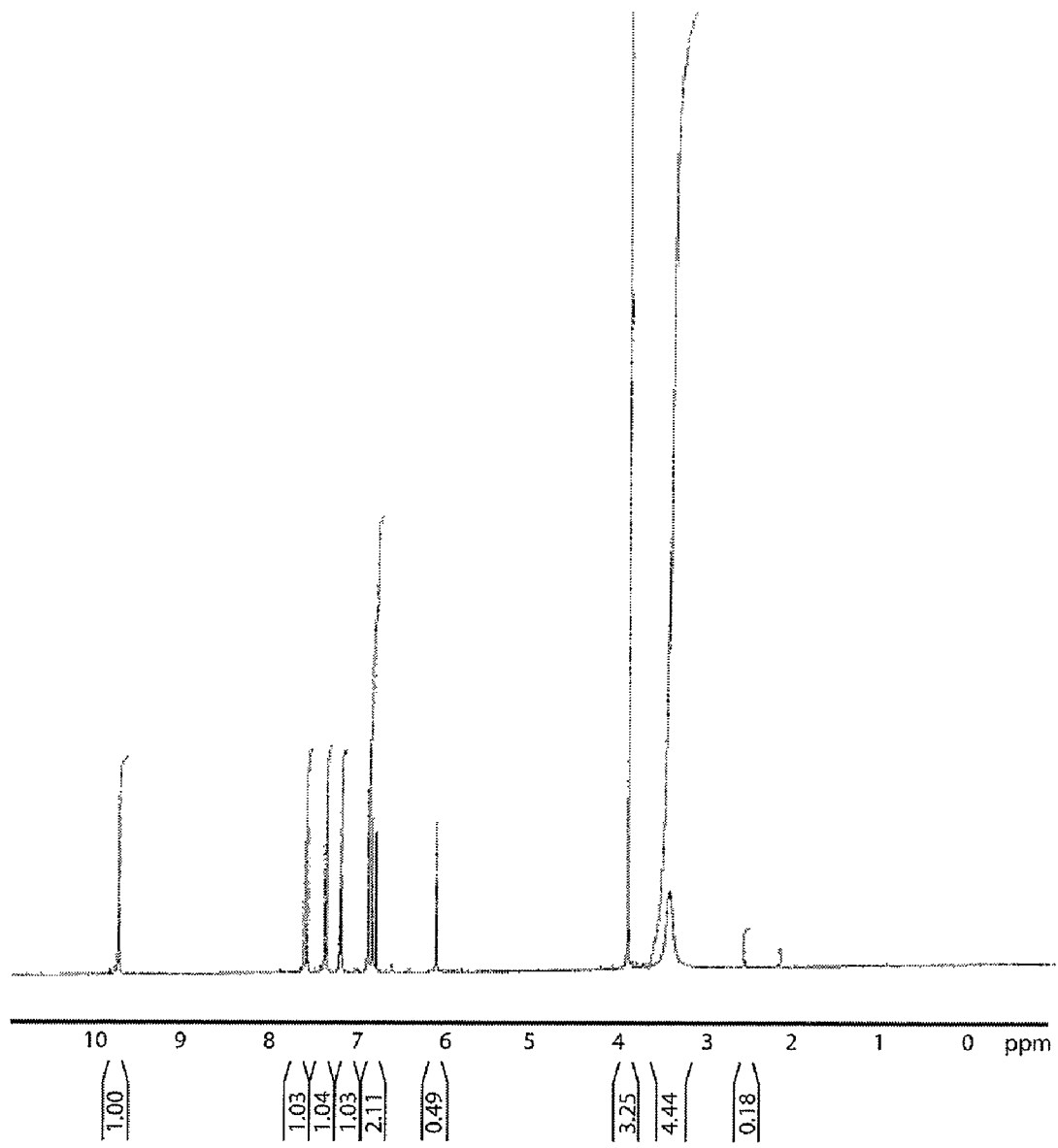
FIG. 2 shows the $^1$H NMR spectra of curcumin obtained through a preferred embodiment of the methods of the present invention. Acquisition Parameters: PROBHD: 5 mm BBO BB-1H; PULPROG: zg30; TD: 65536; SOLVENT: DMSO; NS: 16; DS: 2; SWH: 8278.146 Hz; FIDRES: 0.126314 Hz; AQ: 3.9584243 sec; RG: 181; DW: 60.400 μsec; DE: 6.50 μsec; TE: 300.0° K; D1: 1.00000000 sec; Channel f1: NUCL: 1H; P1: 10.50 μsec; PL1: −2.00 dB; SFO1: 400.1324710 MHz; Processing Parameters: SI: 32768; SF: 400.1299795 MHz; WDW: EM; SSB: 0; LB: 0.30 Hz; GB: 0; PC: 1.00.

The $^1$H NMR spectra of curcumin shows the presence of peaks and relative area of (DMSO-$d_6$): δ 2.55, 3.92, 6.10, 6.79, 6.84, 6.88, 7.20, 7.38, 7.58, 7.62, and 9.73 (FIG. 2). The peak at δ 2.55 is the standard impurity from $d_5$-DMSO in the NMR solvent. The broad peak near δ 3.3 is water impurity from the NMR solvent. The presence of the methoxy groups (—OCH$_3$) on each ring in the structure of curcumin are denoted by δ 3.92. The structural presence of the two OH's on each ring is shown by δ 9.73. It may be noted that the relative area for methoxy protons present is 3.25 and the area of alcohol protons present is 1.00. When the third alcohol, present at δ 6.10, has its relative area of 0.49 added to the other two alcohols, the total area of alcohol protons is 1.49. A determination of structural features is evident in the relative ratio of these two components. For example, the integration value of 3.2 (total area of methoxy groups) can be divided by 1.49 (combined total area of alcohol groups) to equal 2.16, where the relative area of protons present between the methoxy and alcohol groups can be compared with that of the known structure of curcumin. This is indicative of the known structure of curcumin, where the six protons present in two (OCH$_3$) has twice the amount of protons than that of the three total protons from the alcohol groups. The structural data for the olefinic protons present in the middle chain are represented by δ 6.79, 6.84, 6.88 (d), where the doublet of δ 6.88 is from the two identical hydrogens located on each symmetrical carbon next to both rings, δ 6.84 is from the hydrogen attached to the carbon to the right of the carbonyl, and δ 6.79 is located one carbon to the left of the alcohol present on the chain.

Figure 3:
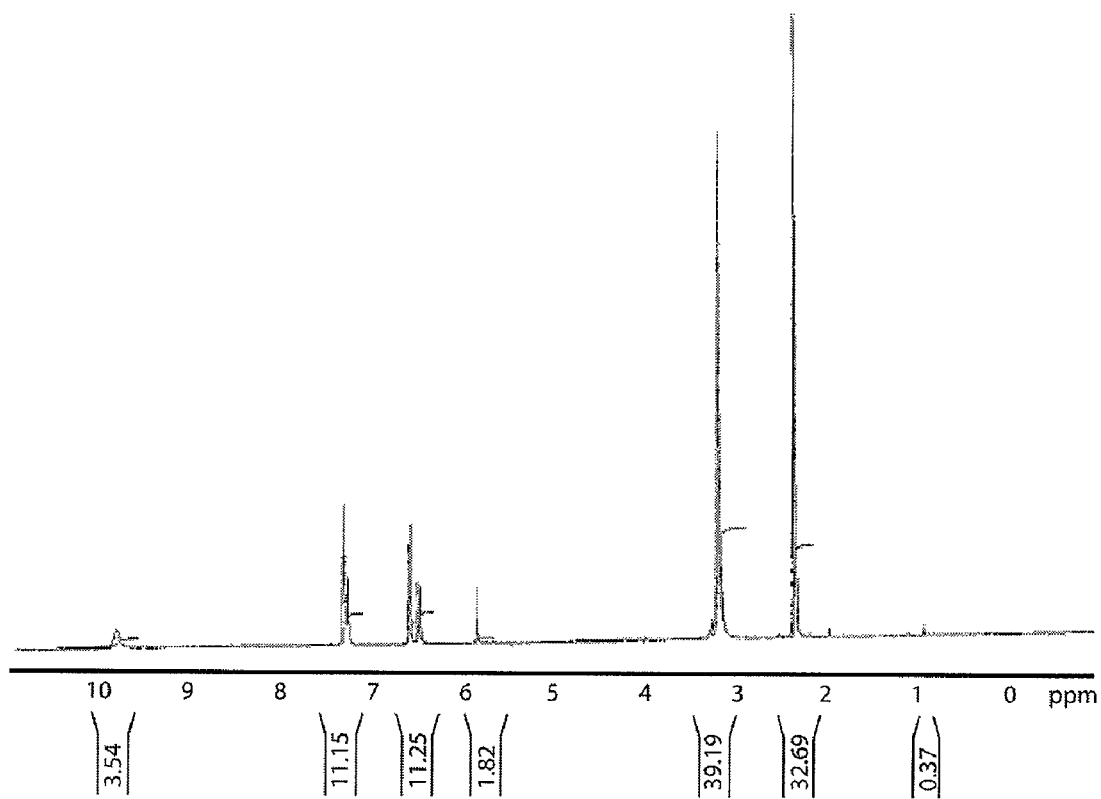
FIG. 3 shows the $^1$H NMR spectra of "Batch 1" of the bisdemethoxycurcumin obtained through a preferred embodiment of the methods of the present invention. Acquisition Parameters: PROBHD: 5 mm BBO BB-1H; PULPROG: zg30; TD: 65536; SOLVENT: DMSO; NS: 16; DS: 2; SWH: 8278.146 Hz; FIDRES: 0.126314 Hz; AQ: 3.9584243 sec; RG: 456.1; DW: 60.400 μsec; DE: 6.50 μsec; TE: 300.0° K; D1: 1.00000000 sec; Channel f1: NUCL: 1H; P1: 10.50 μsec; PL1: −2.00 dB; SFO1: 400.1324710 MHz; Processing Parameters: SI: 32768; SF: 400.1300631 MHz; WDW: EM; SSB: 0; LB: 0.30 Hz; GB: 0; PC: 1.00.
Figure 4:
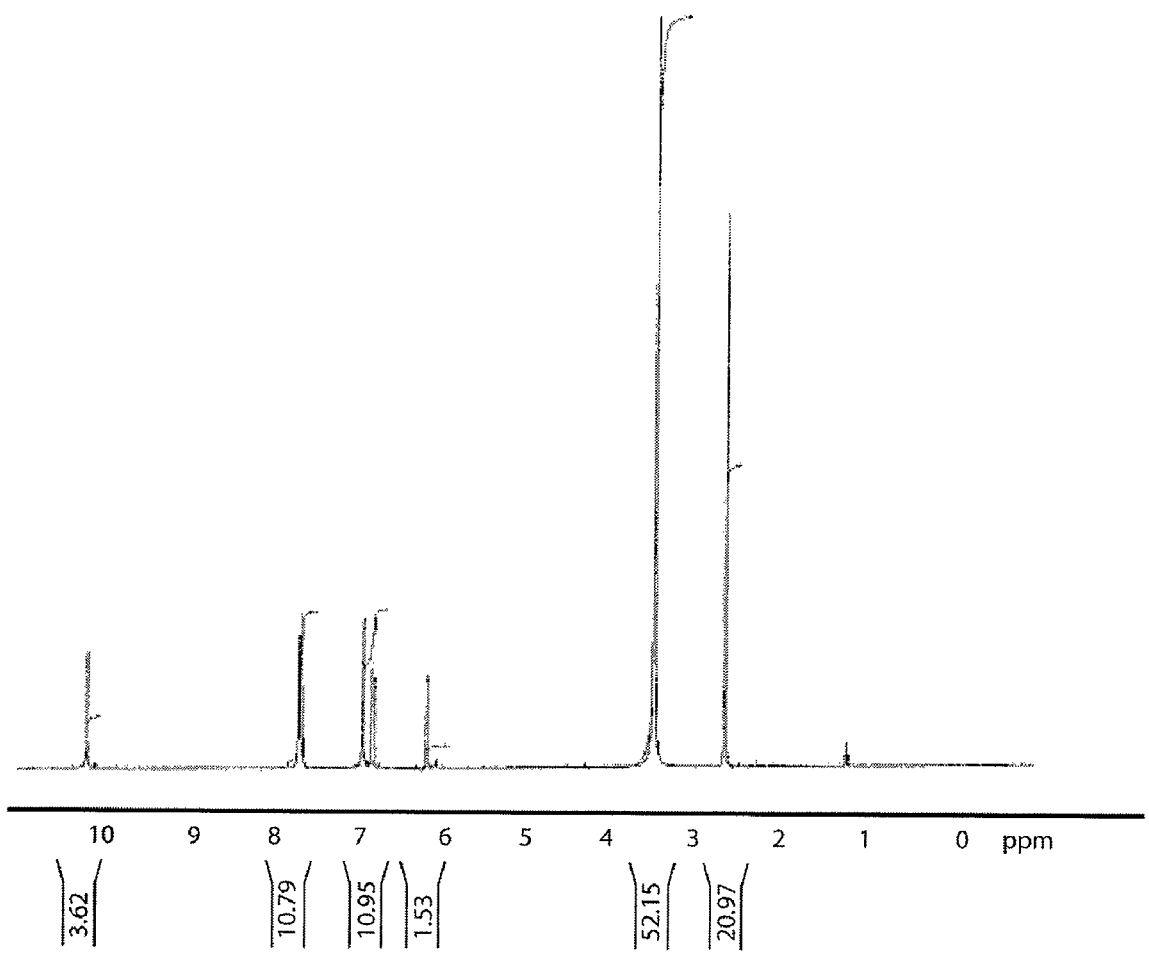
FIG. 4 shows the $^1$H NMR spectra of "Batch 2" of the bisdemethoxycurcumin obtained through a preferred embodiment of the methods of the present invention. Acquisition Parameters: PROBHD: 5 mm BBO BB-1H; PULPROG: zg30; TD: 65536; SOLVENT: DMSO; NS: 16; DS: 2; SWH: 8278.146 Hz; FIDRES: 0.126314 Hz; AQ: 3.9584243 sec; RG: 406.4; DW: 60.400 μsec; DE: 6.50 μsec; TE: 300.0° K; D1: 1.00000000 sec; Channel f1: NUCL: 1H; P1: 10.50 μsec; PL1: −2.00 dB; SFO1: 400.1324710 MHz; Processing Parameters: SI: 32768; SF: 400.1299442 MHz; WDW: EM; SSB: 0; LB: 0.30 Hz; GB: 0; PC: 1.00.
Figure 5:
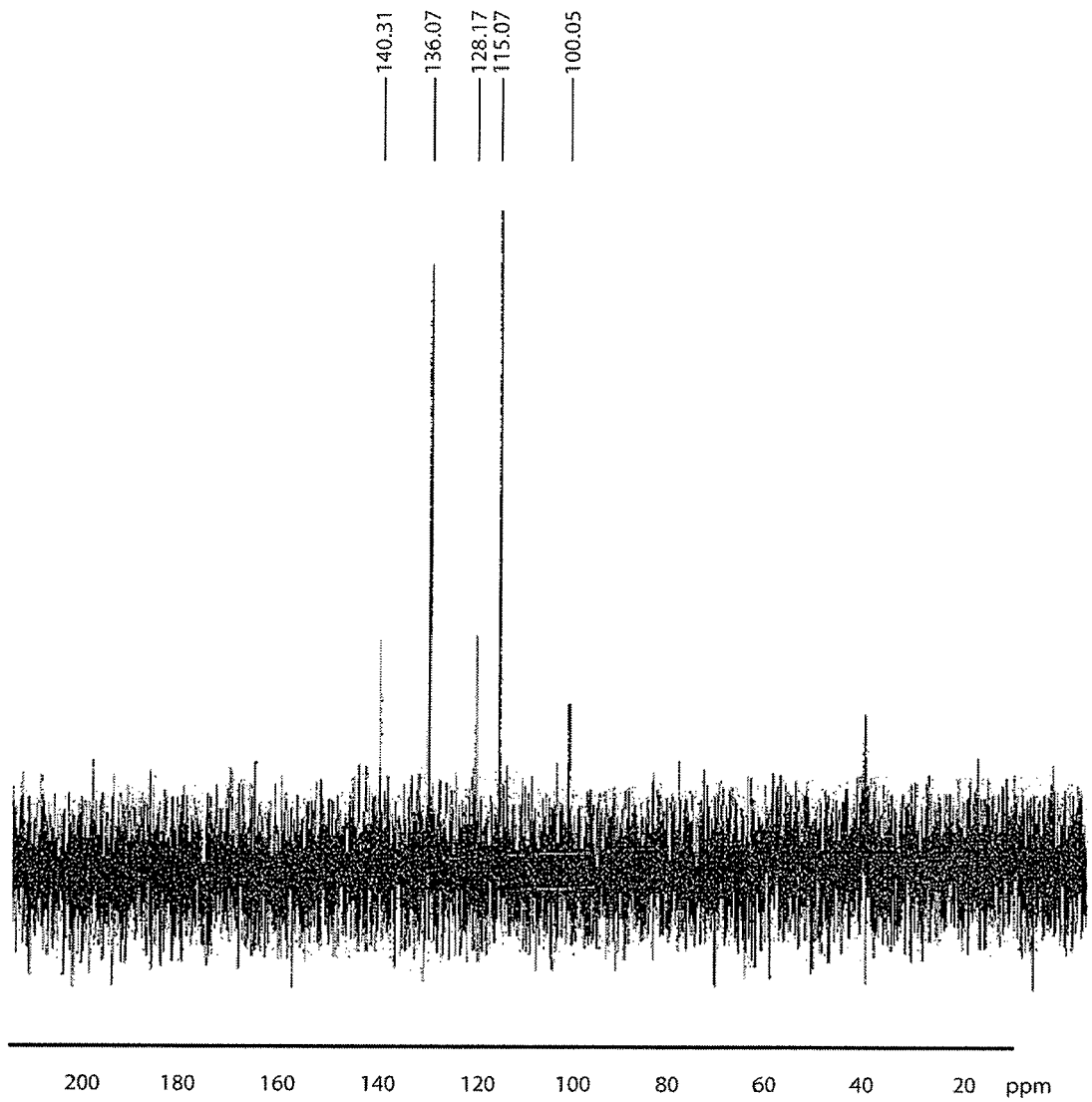
FIG. 5 shows the $^{13}$C NMR DEPT-135 spectra of "Batch 2" of the bisdemethoxycurcumin obtained through a preferred embodiment of the methods of the present invention. Acquisition Parameters: PROBHD: 5 mm BBO BB-1H; PULPROG: dept135; TD: 65536; SOLVENT: DMSO; NS: 256; DS: 4; SWH: 23980.814 Hz; FIDRES: 0.365918 Hz; AQ: 1.3664756 sec; RG: 16384; DW: 20.850 μsec; DE: 6.50 μsec; TE: 300.0° K; CNST2: 145.0000000; D1: 2.00000000 sec; d2: 0.00344828; d12: 0.00002000 sec; DELTA: 0.00000955; Channel f1: NUCL: 13C; P3: 7.50 μsec; p4: 15.00 μsec; PCPD2: 83.00 μsec; PL2: −3.00 dB; PL12: 15.00 dB; SFO2: 400.1316005 MHz; Processing Parameters: SI: 32768; SF: 100.6128193 MHz; WDW: EM; SSB: 0; LB: 1.00 Hz; GB: 0; PC: 1.40.

The spectral analysis of bisdemethoxycurcumin in DMSO-$d_6$ shows δ 2.5 (NMR solvent impurity of DMSO-$d_5$), 3.3 (water impurity), 5.87, 6.54(d), 6.65 (d), 7.44 (s), 7.45 (d), and 9.89 (FIG. 3; FIG. 4). The structural features of bisdemethoxycurcumin are very similar to that of curcumin. The presence of the two alcohols featured symmetrically on the rings is shown at δ 9.89 where the area of 3.54 is in a 2:1 ratio with the presence of the middle hydrogen between the carbonyl and alcohol groups on the carbon rings (δ 5.87) with an area of 1.82. The presence of identical hydrogens symmetrically placed one carbon in from each ring is shown by δ 6.54(d), and the presence of olefinic hydrogens next to both the alcohol and carbonyl groups can be seen in this region of the spectra at δ 6.65(d), 7.44, and 7.45 respectively. The structural determination as bisdemethoxycurcumin is further elucidated from the DEPT-135 spectra of "Batch 2," showing the presence of six total positive peaks for the six different C—H bonds known to be structural components of the compound (FIG. 5).

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of synthesizing a curcuminoid comprising the steps:
   I. combining a solution of an aryl aldehyde with a solution of a pentanedione; wherein:
      (A) said solution of an aryl aldehyde comprises a tri-alkyl borate, a boron oxide, and an alkylamine; and
      (B) said solution of pentanedione is a pentanedione dissolved in a lower alkyl ester; and
   II. incubating said combined solutions, said incubation resulting in said synthesis of said curcuminoid.

2. The method of claim 1, wherein said pentanedione is 2,4-pentanedione.

3. The method of claim 1, wherein said alkylamine is butylamine.

4. The method of claim 1, wherein said tri-alkyl borate is tri-butyl borate.

5. The method of claim 1, wherein said lower alkyl ester is selected from the group consisting of ethyl acetate, propyl acetate, butyl acetate and ethyl butyrate.

6. The method of claim 1, wherein said lower alkyl ester is ethyl acetate.

7. The method of claim 1, wherein said lower alkyl ester is butyl acetate, and said butyl acetate is isobutyl acetate.

8. The method of claim 1, wherein said curcuminoid is curcumin, and:
   (A) said aryl aldehyde is 4-hydroxy-3-methoxybenzaldehyde;
   (B) said tri-alkyl borate is tri-butyl borate;
   (C) said alkylamine is butylamine;
   (D) said pentanedione is 2,4-pantanedione
   (E) said lower alkyl ester is ethyl acetate.

9. The method of claim 1, wherein said curcuminoid is bisdemethoxycurcumin, and:
   (A) said aryl aldehyde is p-hydroxybenzaldehyde;
   (B) said tri-alkyl borate is tri-butyl borate;
   (C) said alkylamine is butylamine;
   (D) said pentanedione is 2,4-pantanedione
   (E) said lower alkyl ester is isobutyl acetate.

* * * * *